United States Patent [19]

Scherm

[11] 4,323,548

[45] Apr. 6, 1982

[54] VAGINAL SUPPOSITORY FOR CONTRACEPTION, HAVING A PREDETERMINED LACTALBUMIN CONTENT

[75] Inventor: Arthur Scherm, Bad Homburg, Fed. Rep. of Germany

[73] Assignee: Merz & Co., Frankfurt, Fed. Rep. of Germany

[21] Appl. No.: 972,228

[22] Filed: Dec. 22, 1978

Related U.S. Application Data

[63] Continuation of Ser. No. 893,187, Apr. 3, 1978, abandoned, which is a continuation of Ser. No. 692,859, Jun. 4, 1976, abandoned.

[30] Foreign Application Priority Data

Jan. 22, 1976 [DE] Fed. Rep. of Germany ....... 2602297

[51] Int. Cl.$^3$ ........................ A61K 9/00; A61K 31/09
[52] U.S. Cl. ........................................ 424/44; 424/78; 424/341; 424/359; 424/DIG. 14; 424/DIG. 15
[58] Field of Search .................. 424/44, 95, 177, 341, 424/78, 359, DIG. 14

[56] References Cited

U.S. PATENT DOCUMENTS

| | | | |
|---|---|---|---|
| 2,467,884 | 4/1949 | Elias | 424/DIG. 14 X |
| 3,875,073 | 4/1975 | Deininger et al. | 424/44 X |
| 3,876,757 | 4/1975 | Scherm | 424/44 |

*Primary Examiner*—Leonard Schenkman
*Attorney, Agent, or Firm*—Gordon W. Hueschen

[57] ABSTRACT

A spermicidally-active vaginal suppository consisting essentially of a solid water-soluble polymeric material which melts at body temperature, for example, a polyethylene glycol, having dispersed therein minor amounts of a spermicide, for example, p-nonylphenoxypolyethoxyethanol, a foaming agent operative when the suppository is dissolved in aqueous media to generate a foam-forming gas, for example, a mixture of a water-soluble bicarbonate and a solid weak acid, and a foam-stabilizing agent which is characterized by containing a surfactant, which is effective to reduce the surface tension of water to less than 45 dynes per centimeter, for example, sodium lauryl sulfate, and lactalbumin.

7 Claims, No Drawings

4,323,548

VAGINAL SUPPOSITORY FOR CONTRACEPTION, HAVING A PREDETERMINED LACTALBUMIN CONTENT

This is a continuation of application Ser. No. 893,187, filed Apr. 3, 1978, now abandoned, which in turn is a continuation of application Ser. No. 692,859, filed June 4, 1976, also now abandoned.

BACKGROUND OF INVENTION

1. Field of Invention

This invention relates to spermicidally-active vaginal suppositories in which the suppository base contains, in addition to a spermicide, a foaming agent and the suppository is so compounded that when it comes in contact with body fluids, the suppository base dissolves or melts and a foam-forming gas is released.

2. Prior Art

The invention is particularly related to improvements in spermicidally-active vaginal suppositories of the character described in U.S. Pat. No. 3,876,757 and British Pat. No. 1,053,615. These patents show spermicidally-active vaginal suppositories consisting essentially of a water-soluble polymeric material which melts at body temperature, having dispersed therein minor amounts of a spermicide, a foaming agent operative when the suppository dissolves in aqueous media to generate a foam-forming gas, and a foam-stabilizing agent.

OBJECTS OF THE INVENTION

It is an object of the invention to provide new and more effective spermicidally-active vaginal suppositories. It is a further object of the invention to provide spermicidally-active vaginal suppositories of the type described having increased stability in the foam produced. A further object of the invention is to avoid the disadvantages of the prior art and to obtain such advantages as will appear as the description proceeds.

BRIEF DESCRIPTION OF THE INVENTION

The invention relates to improvements in spermicidally-active suppositories consisting essentially of a solid water-soluble polymeric material which melts at body temperature having dispersed therein a spermicide, a foaming agent operative when the suppository is dissolved in aqueous media to generate a foam-forming gas, and a foam-stabilizing agent, which improvement is characterized in that the foam-stabilizing agent comprises a surfactant effective to reduce the surface tension of water to less than 45 dynes per centimeter and lactalbumin. The novel foam-stabilizing agent, advantageously, comprises about 2 to about 4 percent sodium lauryl sulfate and an amount of lactalbumin ranging from that effective to impart increased stability to the foam produced up to not more than about 10 percent. Also, the foaming agent, advantageously, comprises a mixture of water-soluble bicarbonate, advantageously, sodium bicarbonate, and a solid weak acid, advantageously, tartaric acid. Other solid weak acids comprise citric acid, boric acid, sodium dihydrogen phosphate and the like. If desired, sulfamic acid may be used as the solid weak acid and, in that case, the bicarbonate can be substituted by a nitrite, for example, ammonium nitrite. Also, such other foaming agents as are known to generate a foam-forming gas when brought into contact with aqueous medium can be used. A sodium bicarbonate and tartaric acid combination has been found particularly advantageous, however, as it produces a homogenous foam and does not impart objectionable acidity to the foam. To this end, the bicarbonate advantageously used is in slight excess of the stoichiometric, say, up to about 10 or 15 percent excess.

The water-soluble polymeric material, advantageously, is a water-soluble polyethylene glycol of suitable chain length or a mixture of different polyethylene glycols such that it melts at body temperature. A particularly preferred mixture of polyethylene glycol comprises polyethylene glycol with a molecular weight of about 1000 and polyethylene glycol with a molecular weight of about 1350 in equal parts. Another useful mixture comprises equal parts of polyethylene glycol 1050 and polyethylene glycol 1250. As uniform polyethylene fraction the fraction within the molecular weight range from 1100 to 1150 is useful. Such polyethylene glycol compositions, upon melting in contact with the vaginal secretions, form a very homogenous foam under the action of the mixture of gas-developing substances.

The surfactant, advantageously, is sodium lauryl sulfate, sodium lauryl ether sulfate, or ethoxylised castor oil as described in U.S. Pat. No. 3,876,757. These surfactants are all effective to reduce surface tension to less than 45 dynes per centimeter and so facilitate and stabilize the formation of the foam. As little as about 2 to about 4 percent of surfactant is effective for this purpose. Any lesser amount which effectively reduces the surface tension could, however, be used and larger amounts, too, could be used but are uneconomical.

According to the invention, the effect of the surfactant in foam-forming and foam-stabilizing is enhanced by incorporating lactalbumin. This, advantageously, is incorporated in that amount which imparts increased stability to the foam which ordinarily will be above about 2 percent up to not more than about 10 percent. Larger amounts could be used, however, as long as they do not adversely affect the character of the suppository base.

A spermicide particularly suitable for use in the composition according to the invention is the p-nonylphenyloxypolyethoxyethanol, which is known per se for contraception. Other useful spermicides according to the invention are triisopropylene phenoxy polyethoxy ethanol or cetylpyridinium bromide. p-Nonylphenyloxypolyethoxyethanol distributes homogenously in the foam as formed, and is distributed equally and evenly over the entire vagina along with development of the foam. Due to the high foam stability, the safe protective effect is maintained over a period of extremely long duration.

In some cases it is useful to add small amounts of parfum oil. Useful parfum oils are Red Rose No. 65,074 sold by DRAGOCO in Holzminden, West-Germany or parfum oil No. 879 sold by Dr. O. Martens, Munchen, West-Germany.

In order to facilitate application of the composition, the contraceptive agent according to the invention is preferably formed in the contours of a longitudinally-shaped body such as a torpedo or an egg, usually having a weight between about 2 and about 5 grams.

For production of the composition of the invention, a mixture of a polyethylene glycol having a suitable molecular weight or a mixture of different polyethylene glycol fractions, the spermicide, the foaming agent, the foam stabilizer and, if need be, certain additional substance (parfum oil) is melted at an elevated temperature, and the various components intimately mixed together by stirring. Without cooling, the liquid mixture is subsequently cast into desired, e.g., egg shapes, and cooled to solidify the mass. A more detailed description of the process according to the invention is disclosed in the examples. The mixture preferably contains about 65 to about 85 percent of polyethylene glycol, about 10 to about 20 percent foaming agent, about 4 to about 14 percent of foam stabilizer, of which between about 2 and about 4 percent is surfactant and between about 2 and about 10 percent is lactalbumin, and about 2 to about 5 percent of spermicide.

The parts and percentages are by weight unless otherwise specified.

PREPARATION I 108.675 g polyethylene glycol 1000 and 108.675 g polyethylene glycol 1350 are intimately mixed by stirring or kneading with 6.12 g p-nonylphenoxypolyethoxyethanol, 18.36 g sodium bicarbonate, 16.29 g tartaric acid, and 6.4 g sodium lauryl sulfate at 50° C. At this temperature the pourable mixture is cast into egg-shaped molds and is cooled to ambient temperature. The weight of the vaginal ovulae amounted to 3 g.

EXAMPLE 1

Part A

Following the procedure of PREPARATION I, there was included along with the 6.4 g sodium lauryl sulfate, 5.4 g lactalbumin to give a spermicidally-active vaginal suppository (weight: 3 g), having the following composition:

| | |
|---|---|
| Polyethylene glycol 1000 | 80.54% |
| Polyethylene glycol 1350 | |
| p-Nonylphenoxypolyethoxyethanol | 2.26% |
| Sodium bicarbonate | 12.83% |
| Tartaric acid | |
| Sodium lauryl sulfate | 2.37% |
| Lactalbumin | 2.0% |

Part B

The procedure of Part A was followed except that the lactalbumin was increased to give 5% lactalbumin.

Part C

The procedure of Part A was followed except that the lactalbumin was increased to give 7% lactalbumin.

Part D

The procedure of Part A was followed except that the lactalbumin was increased to give 10% lactalbumin.

PREPARATION II 95.87 g polyethylene glycol 1000 and 95.87 g polyethylene glycol 1350 are intimately mixed by stirring or kneading with 13.5 g p-nonylphenoxypolyethoxyethanol, 27.0 g sodium bicarbonate, 23.4 g tartaric acid, and 5.0 g sodium lauryl sulfate at 50° C. At this temperature the pourable mixture is cast into egg-shaped molds and is cooled to ambient temperature. The weight of the vaginal ovulae amounted to 3 g.

EXAMPLE 2

Part A

Following the procedure of PREPARATION II, but including along with the 5.0 g sodium lauryl sulfate, 8.06 g lactalbumin, a spermicidally-active vaginal suppository (weight: 3g), of the following composition was obtained:

| | |
|---|---|
| Polyethylene glycol 1000 | 71.36% |
| Polyethylene glycol 1350 | |
| p-Nonylphenoxypolyethoxyethanol | 5.02% |
| Sodium bicarbonate | 18.76% |
| Tartaric acid | |
| Sodium lauryl sulfate | 1.86% |
| Lactalbumin | 3.0% |

Part B

The procedure of Part A was followed except that the lactalbumin was increased to give 7% lactalbumin.

Part C

The procedure of Part A was followed except that the lactalbumin was increased to give 10% lactalbumin.

PREPARATION III 7.74 g p-nonylphenoxypolyethoxyethanol is dissolved in a melt composed of 99.71 g polyethylene glycol 1000 and 99.71 g polyethylene glycol 1350. Subsequently, 18.36 g sodium bicarbonate, 16.29 g tartaric acid and 10.80 g sodium lauryl sulfate are suspended in the said melt. The melt is cast into molds of 3 g each.

EXAMPLE 3

Part A

Following the procedure of PREPARATION III but including along with the 10.80 g sodium lauryl sulfate, 19.01 g lactalbumin, the following spermicidally-active vaginal suppository (weight: 3 g), was obtained:

| | |
|---|---|
| Polyethylene glycol 1000 | 73.42% |
| Polyethylene glycol 1350 | |
| P-Nonylphenoxypolyethoxyethanol | 2.85% |
| Sodium bicarbonate | 12.75% |
| Tartaric acid | |
| Sodium lauryl sulfate | 3.98% |
| Lactalbumin | 7.0% |

Part B

The procedure of Part A was followed except that the lactalbumin was increased to give 10% lactalbumin.

The foregoing examples were compared with the corresponding preparations to determine dissolution and foam stability. In each test a suppository was placed in 0.7 milliliters of water. The time it took the suppository to dissolve was noted, as was the height of the foam in centimeters after one hour. The results obtained are tabulated in the following table.

TABLE

| | Preparation I | Example I | | | | Preparation II | Example II | | | Preparation III | Example III | |
|---|---|---|---|---|---|---|---|---|---|---|---|---|
| | | A | B | C | D | | A | B | C | | A | B |
| Change by the addition of lactalbumin | | | | | | | | | | | | |
| Lactalbumin g/3g vaginal uvula | — | 0.06 = 2% | 0.15 = 5% | 0.21 = 7% | 0.3 = 10% | — | 0.09 = 3% | 0.21 = 7% | 0.3 = 10% | — | 0.21 = 7% | 0.3 = 10% |
| pH value | 6.0 | 5.8 | 6.3 | 5.4 | 6.2 | 5.0 | 5.4 | 6.0 | 6.1 | 4.3 | 6.0 | 6.2 |
| Dissolution time (min) in 0.7 ml water | 13 | 15 | 17 | 17 | 18 | 16 | 17 | 20 | 15 | 21 | 20 | |
| Foam stability as foam level in cm after 1h | 1.4 | 1.4 | 3.0 | 3.0 | 3.4 | 1.4 | 1.6 | 3.0 | 3.5 | 1.0 | 3.0 | 3.5 |

It will be observed that the inclusion of lactalbumin increased the dissolution time and gave increased stability to the foam. It is well recognized in this art that the longer it takes the suppository to dissolve and the longer a stable foam obtains, the more effective the suppository is for its intended purpose.

It is to be understood that the invention is not to be limited to the exact details of operation or structure shown and described, as obvious modifications and equivalents will be apparent to one skilled in the art.

I claim:

1. A foam-producing vaginal suppository consisting essentially of about 65 to about 85 percent by weight of a solid water-soluble polyethylene glycol material which melts at body temperature, having dispersed therein minor amounts of a spermicide, about 10 to about 20 percent by weight of a foaming agent comprising a mixture of a water-soluble bicarbonate and a solid weak acid, operative when the suppository is dissolved in aqueous medium to generate a foam-forming gas, and a foam-stabilizing agent, characterized in that the foam-stabilizing agent comprises about 2 to about 4 percent by weight of a surfactant, which is effective to reduce the surface tension of water to less than 45 dynes per centimeter, and lactalbumin in an amount ranging from that amount which is effective to impart increased stability to the foam produced up to and not more than about 10 percent by weight.

2. A spermicidally-active vaginal suppository according to claim 1, in which the foam-stabilizing agent comprises sodium lauryl sulfate.

3. A spermicidally-active vaginal suppository according to claim 1, in which the foaming agent comprises a mixture of sodium bicarbonate and tartaric acid.

4. A spermicidally-active vaginal suppository according to claim 1, in which the amount of spermicide ranges from about 2 to about 5 percent, and the amount of foam-stabilizing agent from about 4 to about 14 percent.

5. A spermicidally-active vaginal suppository according to claim 4, in which the foam-stabilizing agent contains from about 2 to about 4 percent sodium lauryl sulfate and an amount of lactalbumin ranging from that effective to impart increased stability to the foam produced up to and not more than about 10 percent by weight.

6. A spermicidally-active vaginal suppository according to claim 5; in which the water-soluble polyethylene glycol material is a mixture of polyethylene glycols and the spermicide is p-nonylphenoxypolyethoxyethanol.

7. A spermicidally-active vaginal suppository according to claim 6, in which the foaming agent comprises a mixture of sodium bicarbonate and tartaric acid.

* * * * *

UNITED STATES PATENT AND TRADEMARK OFFICE
CERTIFICATE OF CORRECTION

PATENT NO. : 4,323,548

DATED : April 6, 1982

INVENTOR(S) : Arthur Scherm

It is certified that error appears in the above—identified patent and that said Letters Patent is hereby corrected as shown below:

Col. 6, TABLE, column "C" under "Example II"; delete "15" and insert — 20 —
Col. 6, TABLE, column titled "PREPARATION III" third figure down; delete "21" and insert — 15 —
Col. 6, TABLE, column "A" under "Example III"; delete "20" and insert — 21 —
Col. 6, TABLE, column "B" under "Example III", one line below "6.2" insert — 20 —

Signed and Sealed this

Twentieth Day of July 1982

[SEAL]

Attest:

GERALD J. MOSSINGHOFF

Attesting Officer    Commissioner of Patents and Trademarks